United States Patent [19]

Baldwin et al.

[11] Patent Number: 5,766,963
[45] Date of Patent: Jun. 16, 1998

[54] COMBINATION HYDROXYPROPYLAMINE LIBRARY

[75] Inventors: John J. Baldwin, Gwynedd Valley, Pa.; Ian Henderson, Plainsboro; Frank S. Waksmunski, South River, both of N.J.

[73] Assignee: Pharmacopeia, Inc., Princeton, N.J.

[21] Appl. No.: 592,654

[22] Filed: Jan. 26, 1996

[51] Int. Cl.$^6$ .................. G01N 33/543; G01N 33/544; G01N 33/545; G01N 33/551
[52] U.S. Cl. .................. 436/518; 436/501; 436/523; 436/524; 436/527; 436/528; 436/529; 436/530; 436/531; 435/4
[58] Field of Search ............... 435/4, 7.1, 7.21, 435/7.71, 7.8, 7.93, 7.4, 7.7, 7.9; 436/501, 518, 523, 524, 527–531

[56] References Cited

U.S. PATENT DOCUMENTS

| | | | |
|---|---|---|---|
| 4,383,031 | 5/1983 | Boguslaski et al. | 435/7 |
| 5,525,735 | 6/1996 | Gallop et al. | 548/533 |
| 5,573,905 | 11/1996 | Lerner et al. | 435/6 |

OTHER PUBLICATIONS

Brenner & Lerner, "Encoded Combinatorial Chemistry", Proc. Nat. Acad. Sci. USA 89, 5381–5383 (1992).
Burbaum et al. "A Paradigm for Drug Discovery Employing Encoded Combinatorial Libraries", Proc. Natl. Acad. Sci USA 92, 6027–6031 (1995).

*Primary Examiner*—Ponnathapura Achutamurthy
*Attorney, Agent, or Firm*—Heslin & Rothenberg, PC

[57] ABSTRACT

A combinatorial library is disclosed which is represented by Formula

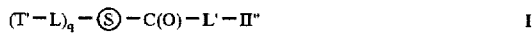

I

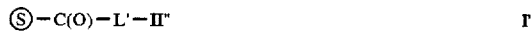

I' or wherein:

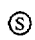

is a solid support; T'-L- is an identifier residue; and -L'-II' is a ligand/linker residue. This library contains hydroxypropylamines of the formula:

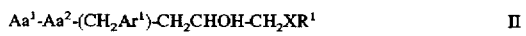

II wherein:

$Aa^1$ and $Aa^2$ is each an amino acid joined to each other through an amide bond;
$Ar^1$ is an aromatic ring system;
—$CH_2Ar^1$ is attached to N on $Aa^2$; and
$R^1$ is H, $C_{1-20}$ alkyl, alkenyl, alkynyl, aryl, heteroaryl, aryl or heteroaryl fused to a 3- or 4-membered moiety to form a non-aromatic second ring, or substituted $C_{1-20}$ alkyl, alkenyl, or alkynyl.

6 Claims, No Drawings

1

COMBINATION HYDROXYPROPYLAMINE LIBRARY

CROSS-REFERENCE

Lawn Assay for Compounds That Affect Enzyme Activity or Bind to Target Molecules, U.S. Ser. No. 08/553,056, filed Nov. 3, 1995, is incorporated herein by reference.

All patents and other references cited herein are hereby incorporated by reference.

BACKGROUND OF THE INVENTION

There is interest in methods for the synthesis of large numbers of diverse compounds which can be screened for various possible physiological or other activities. Techniques have been developed in which one adds individual units sequentially as part of the chemical synthesis to produce all or a substantial number of the possible compounds which can result from all the different choices possible at each sequential stage of the synthesis. For these techniques to be successful, it is necessary for the compounds to be amenable to methods by which one can determine the structure of the compounds so made. Brenner and Lerner (*PNAS USA* 81: 5381–83 (1992)) and WO 93/20242, for example, describe a synthesis wherein oligonucleotides are produced in parallel with and are chemically linked as genetic tags to oligopeptides as the compounds of interest. WO 93/06121 teaches methods for particles-based synthesis of random oligomers wherein identification tags on the particles are used to facilitate identification of the oligomer sequence synthesized. A detachable tagging system is described in Ohlmeyer et al., *Proc. Natl. Acad. Sci. USA*, 90, 10922–10926, Dec. 1993.

SUMMARY OF THE INVENTION

The present invention relates to a combinatorial library of compounds encoded with tags and to the use of this library in assays to discover biologically active compounds. The present invention also relates to a library of hydroxypropylamine compounds containing two amino acid residues and a heteroatom-substituted hydroxypropyl residue and using this library to identify biologically active members by screening in bioassays.

DETAILED DESCRIPTION OF THE INVENTION

The combinatorial chemical library of the present invention is represented by Formula I:

$$(T-L)_q-\text{\textcircled{S}}-C(O)-L'-II \qquad I$$

wherein:

$\text{\textcircled{S}}$ is a solid support;

T'-L- is an identifier residue;

-L'-II is a linker/ligand residue; and q is 2-30; and

II' is $$-Aa^1-Aa^2-(CH_2Ar^1)-CH_2CHOH-CH_2XR^1$$

wherein:

$Aa^1$ and $Aa^2$ are each an amino acid joined to each other through an amide bond with the provisos that $Aa^1$ cannot contain a linear chain of 3, 4, or 5 atoms which separate the carboxyl carbonyl from the amino group of $Aa^a$, and $Aa^2$ cannot be an α-amino acid;

$Ar^1$ is aryl or heteroaryl;

$-CH_2Ar^1$ is attached to N on $Aa^2$;

$R^1$ is H, $C_{1-20}$ alkyl, alkenyl, alkynyl, aryl, heteroaryl, substituted aryl or heteroaryl, aryl or heteroaryl fused to a 3- or 4-membered moiety to form a non-aromatic second ring, or substituted $C_{1-20}$ alkyl, alkenyl, or alkynyl; and X is O, N-loweralkyl, S, S(O), or $S(O)_2$.

Preferred libraries of Formula I are those wherein T'-L- is of the Formula

III wherein:

n=3-12;

Ar is halophenyl; and q is 3-12.

Other preferred libraries of Formula I are those wherein -L'- is (a)

wherein the left-hand bond as shown is the point of attachment to the solid support and the right hand bond is the point of attachment to the ligand.

More-preferred libraries of Formula I are those wherein in Formula III: 1) n=3-12 and Ar is pentachlorophenyl; or 2) n=5-6 and Ar is 2,4,6-trichlorophenyl.

Depending on the choice of L' (see Table 1), the ligands of Formula II may be detached by photolytic, oxidative, acidic, basic, or other cleavage techniques. For example, when -L'- is (a), acidic cleavage may be represented by:

$$I \xrightarrow{H^+} (T-L)_q-\text{\textcircled{S}}-C(O)-L'' + II'OH$$

wherein L'' is the residue from L' and II'OH is II:

$$Aa^a-Aa^2-(CH_2Ar^1)-CH_2CHOH-CH_2XR^1 \qquad II$$

A preferred embodiment of the invention is a library of Formula I wherein:

$Aa^1$ is selected from the seven residues of the amino acids of Table 1-1;

$Aa^2$ is selected from the 15 residues of the amino acids of Table 1-2;

$Ar^1$ is selected from the 31 aryl and heteroaryl residues of the aldehydes of Table 1-3;

$R^1$ is selected from the 31 alkyl, aryl, arylalkyl, and heteroaryl residues of epoxides of Table 1-4; and X is O or S.

One embodiment of the invention is the use of the combinatorial library of Formula I in assays to discover biologically active compounds (ligands) of Formula II. Thus, an aspect of the invention is a method of identifying a compound having a desired characteristic which comprises synthesizing a combinatorial library of Formula I and testing the library of Formula I, either attached to the solid support or detached therefrom, in an assay which identifies compounds of Formula II having the desired characteristic. Another embodiment of the invention is a method of identifying a compound having a desired characteristic which comprises testing the library of Formula I, either attached to the solid support or detached therefrom, in an assay which identifies compounds of Formula II having the desired characteristic. A further embodiment of the invention is determining the structure of any compound so identified.

It is within the scope of the present invention that the determination of the structures of compounds having the desired characteristic can be accomplished by decoding the tags (represented by T'-L- in Formula I) or, alternatively, by deconvolution of the library (Smith et al., *BioMed. Chem. Lett.*, 4, 2821 (1994); Kurth et al., *J. Org. Chem.*, 59, 5862 (1994); Murphy et al., *J. Am. Chem. Soc.*, 117, 7029 (1995); Cambell et al., *J. Am. Chem. Soc.*, 117, 5381 (1995); and Erb et al., *Proc. Nat. Acad. Sci. USA*, 91, 11422 (1994)). In the latted case, the library of the present invention is represented by Formula I'

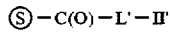

wherein the symbols are as defined for Formula I.

Another embodiment of the invention is a method of synthesizing a library of Formula Ia which comprises reacting a compound of Formula 4

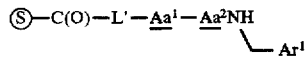

with an epoxide of the formula

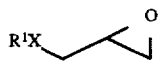

dissolved in a suitable solvent such as acetonitrile or a lower alcohol, e.g. isopropanol, at 25°–82° C. to produce a library of Formula Ia

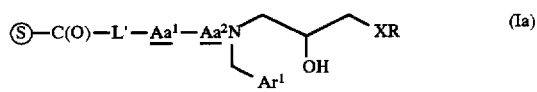

wherein:
HO-Aa"-H=Aa" with the HO— incorporated into the carboxyl group of the amino acid Aa" and the —H attached to the nitrogen of amino acid Aa" and N of amino acid Aa² is depicted to show the point of attachment of —(CH₂)—Ar¹, and n=1 or 2.

Another embodiment of the invention is a combinatorial library of chemical intermediates of the formulae

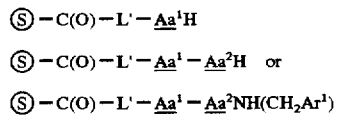

which are useful in the preparation of libraries of Formula I or I'.

Another embodiment of the invention is a method of preparing a library of compounds of the formula 4:

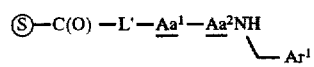

which comprises:

1) reacting a compound of the formula 3:

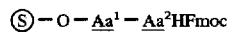

with piperidine/DMF at room temperature for about 1 hr;

2) reacting the product of step 1 with a carboxaldehyde reagent of formula $Ar^1$ CHO, dissolved in toluene, at room temperature for about 15 hr to produce an imine; and 3) suspending the imine of step 2 in methanol with sodium cyanoborohydride at room temperature for about 4 hr to produce a library of compounds 4.

Another embodiment of the invention is the use of divinylbenzene-cross-linked, polyethyleneglycol-grafted polystyrene beads optionally functionalized with amino groups (for example, TentaGel® S $NH_2$, Rapp Polymere) as the solid supports for constructing a combinatorial library of Formula I or I'.

Definitions

The following abbreviations have the indicated meaning:
Bn=benzyl
c-=cyclo
DEAD=diethylazodicarboxylate
DCM=dichloromethane=methylene chloride
DIC=diisopropylcarbodiimide
DMAP=4-N,N-dimethylaminopyridine
DMF=N,N-dimethylformamide
DVB=1,4-divinylbenzene
FACS=fluorescence activated cell sorting
Fmoc=9-fluorenylmethoxycarbonyl
GC=gas chromatography
HOBt=hydroxybenzotriazole
m-=meta
Me=methyl
Mtr=4-methoxy-2,3,6-trimethylbenzenesulfonyl
$NaBH^3CN$=sodium cyanoborohydride
PEG=polyethylene glycol
Ph=phenyl
r.t.=room temperature
sat'd=saturated
s-=secondary
t-=tertiary
TFA=trifluoroacetic acid
THF=tetrahydrofuran
Thy=thienyl Alkyl is intended to include linear, branched, or cyclic hydrocarbon structures and combinations thereof. "Lower alkyl" means alkyl groups of from 1 to 8 carbon atoms. Examples of lower alkyl groups include methyl, ethyl, propyl, isopropyl, butyl, s- and t-butyl, pentyl, hexyl, octyl, cyclopropylethyl, and the like. "Lower cycloalkyl" includes cycloalkyl groups of from 3 to 8 carbon atoms. Examples of lower cycloalkyl groups include c-propyl, c-butyl, c-pentyl, 2-methylcyclopropyl, cyclopropylmethyl, norbornyl, and the like.

"Alkenyl" is $C_2$–$C_8$ alkenyl of a linear, branched, or cyclic ($C_5$–$C_6$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl, and the like.

"Alkynyl" is $C_2$–$C_8$ alkynyl of a linear or branched configuration and combinations thereof. Examples of alkenyl groups include ethyne, propyne, butyne, pentyne, 3-methyl-1-butyne, 3,3-dimethyl-1-butyne, and the like.

"Alkoxy" means alkoxy groups of from 1 to 8 carbon atoms of a straight, branched, or cyclic configuration and combinations thereof. Examples of alkoxy groups include methoxy, ethoxy, propoxy, isopropoxy, cyclopropyloxy, cyclohexyloxy, and the like.

"Acylamino" means acylamino groups of from 1 to 8 carbon atoms of a straight, branched or cyclic configuration and combinations thereof. Examples of acylamino groups are acetylamino, butylamino, cyclohexylamino, and the like.

Halogen includes F, Cl, Br, and I.

"Halophenyl" means phenyl substituted by 1–5 halogen atoms. Halophenyl includes pentachlorophenyl, pentafluorophenyl, and 2,4,6-trichlorophenyl.

"Aryl" and "heteroaryl" mean a 5- or 6-membered aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or a tricyclic 13- or 14-membered aromatic or heteroaromatic ring system containing 0–3 heteroatoms selected from O, N, and S; each of which rings is optionally substituted with 1–3 substituents selected from lower alkyl, alkenyl, alkynyl, substituted loweralkyl, substituted alkenyl, substituted alkynyl,=O, $NO_2$, halogen, hydroxy, alkoxy, cyano, $NR^2R^2$, acylamino, phenyl, benzyl, phenoxy, benzyloxy, heteroaryl, and heteroaryloxy, each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, alkoxy, cyano, phenyl, phenoxy, benzyl, benzyloxy, caboxamido, heteroaryl, heteroaryloxy, $NO_2$, and $NR^2R^2$;

$R^2$ is H or lower alkyl.

The aromatic 6- to 14-membered carbocyclic rings include benzene, naphthalene, indane, tetralin, and fluorene and the 5- to 10-) membered aromatic heterocyclic rings include imidazole, pyridine, indole, thiophene, benzopyranone, thiazole, furan, benzimidazole, quinoline, isoquinoline, quinoxaline, pyrimidine, pyrazine, tetrazole, and pyrazole.

"Substituted" alkyl, alkenyl, or alkynyl means alkyl, alkenyl, or alkynyl wherein up to three H atoms on each C therein are replaced by halogen, hydroxy, loweralkoxy, carboxy, carboalkoxy, carboxamido, cyano, carbonyl, $NO_2$, $NR^2R^2$, alkylthio, sulfoxide, sulfone, acylamino, amidino, phenyl, benzyl, heteroaryl, phenoxy, benzyloxy, heteroaryloxy, and substituted phenyl, benzyl, heteroaryl, phenoxy, benzyloxy, and heteroaryloxy.

$Aa^1$ and $Aa^2$ are intended to include the racemates and all optical isomers thereof. The amino acid sidechains of $Aa^1$ and $Aa^2$ are, for example, methyl (alanine), hydroxymethyl (serine), phenylmethyl (phenylalanine), thiomethyl (cysteine), carboxyethyl (glutamic acid), etc. The primary and secondary amino acids are intended to include alanine, asparagine, N-β-trityl-asparagine, aspartic acid, aspartic acid-β-t-butyl ester, arginine, $N^g$-Mtr-arginine, cysteine, S-trityl-cysteine, glutamic acid, glutamic acid-γ-t-butyl ester, glutamine, N-γ-trityl-glutamine, glycine, histidine, $N^{im}$-trityl-histidine, isoleucine, leucine, lysine, $N^ε$-Boc-lysine, methionine, phenylalanine, proline, serine, O-t-butyl-serine, threonine, tryptophan, $N^{in}$-Boc-tryptophan, tyrosine, valine, sarcosine, L-alanine, chloro-L-alanine hydrochloride, 2-aminoisobutyric acid, 2-(methylamino) isobutyric acid, D,L-3-aminoisobutyric acid, (R)-(–)-2-aminoisobutyric acid, (S)-(+)-2-aminoisobutyric acid, D-t-leucine, L-t-leucine, D-norvaline, L-norvaline, L-2-amino-4-pentenoic acid, D-isoleucine, L-isoleucine, D-norleucine, 2,3-diaminopropionic acid monohydrochloride, L-norleucine, D,L-2-aminocarprylic acid, β-alanine, D,L-3-aminobutyric acid, 4-aminobutyric acid, 4-(methylamino) butyric acid hydrochloride, 5-aminovaleric acid, 5-aminocaproic acid, 7-aminoheptanoic acid, 8-aminocaprylic acid, 11-aminodecanoic acid, 12-aminododecanoic acid, carboxymethoxylamine hemihydrate, D-serine, D-homoserine, L-homoserine, D-allothreonine, L-allothreonine, D-threonine, L-threonine, D,L-4-amino-3-hydroxybutyric acid, D,L-3-hydroxynorvaline, (3S,4S)-(–)-statine, 5-hydroxy-D,L-lysine hydrochloride, 5-aminoleucinic acid hydrochloride, 1-amino-1-cyclopropanecarboxylic acid, 1-amino-1-cyclopentanecarboxylic acid, 1-amino-1-cyclohexanecarboxylic acid, 5-amino- 1,3-cyclohexadiene-1-carboxylic acid hydrochloride, 2-amino-2-norbornanecarboxylic acid, (S)-(–)-2-azetidinecarboxylic acid, cis-4-hydroxy-D-proline, cis-4-hydroxy-L-proline, trans-4-hydroxy-L-proline, 3,4-dehydro-D,L-proline, 3,4-dehydro-L-proline, D-pipecolinic acid, L-pipecolinic acid, nipecotic acid, isonipecotic acid, mimosine, 2,3-diaminopropionic acid monohydrobromide, D,L-2,4-diaminobutyric acid dihydrochloride, (S)-(+)-diaminobutyric acid hydrochloride, D-ornithine hydrochloride, L-ornithine hydrochloride, 2-methylornithine hydrochloride monohydrate, N-ε-methyl-L-lysine hydrochloride, N-methyl-D-aspartic acid monohydrate, D,L-2-methylglutamic acid hemihydrate, D,L-2-aminoadipic acid, D-2-aminoadipic acid, L-2-aminoadipic acid, (±)-3-aminoadipic acid, D-cysteine hydrochloride monohydrate, D-penicillamine, L-penicillamine, D,L-homocysteine, S-methyl-L-cysteine, L-methionine, D-ethionine, L-ethionine, S-carboxymethyl-L-cysteine, (S)-(+)-2-phenylglycine, (R)-(–)-2-phenylglycine, N-phenylglycine, N-(4-hydroxyphenyl) glycine, D-phenylalanine, (S)-(–)indoline-2-carboxylic acid, α-methyl,D,L-phenylalanine, β-methyl-D,L-phenylalanine hydrochloride, D-homophenylalanine, L-homophenylalanine, D,L-2-fluorophenylglycine, D,L-2-fluorophenylalanine, D,L-3-fluorophenylalanine, D,L-4-fluorophenylalanine, D,L-4-chlorophenylalanine, L-4-chlorophenylalanine, 4-bromo-D,L-phenylalanine, 4-iodo-D-phenylalanine, 3,3',5-triiodoL-thyronine, (+)-3,3',5-triiodo-L-thyronine sodium salt, D-thyronine, L-thyronine, D,L-m-tyrosine, D-4-hydroxyphenylglycine, D-tyrosine, L-tyrosine, o-methyl-L-tyrosine, 3-fluoro-D,L-tyrosine, 3-iodo-L-tyrosine, 3-nitro-L-tyrosine, 3,5-diiodo-L-tyrosine dihydrate, D,L-dopa, L-dopa, 2,4,5-trihydroxyphenyl-D,L-alanine, 3-amino-L-tyrosine dihydrochloride monohydrate, 4-amino-D-phenylalanine hydrate, 4-amino-L-phenylalanine hydrate, 4-amino-D,L-phenylalanine hydrate, 4-nitro-L-phenylalanine monohydrate, 4-nitro-D,L-phenylalanine, 3,5-dinitro-L-tyrosine monohydrate, D,L-α-methyltyrosine, L-α-methyltyrosine, (–)-3-(3,4-dihydroxyphenyl)-2-methyl-L-alanine sesquihydrate, D,L-threo-3-phenylserine hydrate, D,L-DOPS, trans-4-(aminomethyl)cyclohexane carboxylic acid, 4-(aminomethyl)benzoic acid, D,L-3-aminobutyric acid, 3-aminocyclohexane carboxylic acid, cis-2-amino-1-cyclohexane carboxylic acid, γ-amino-β-(p-chlorophenyl) butyric acid (Baclofen), D,L-3-aminophenylpropionic acid, 3-amino-3-(4-chlorophenyl)propionic acid, 3-amino-3-(2-nitrophenyl)propionic acid, and 3-amino-4,4,4-trifluorobutyric acid $Ar^1$ is intended to include phenyl, thienyl, furanyl, pyridyl, pyrimidyl, naphthyl, fluorenyl, biphenyl, phenoxyphenyl, and benzyloxyphenyl.

It is intended that the definitions of any substituent or symbol (e.g., $Aa^1$, $Aa^2$, etc.) in a particular molecule be independent of its definitions elsewhere in the molecule.

Thus, "Aa¹-Aa²-(CH₂Ar¹)-represents HO₂CCH(isopropyl)NHCOCH₂CH₂N(CH₂Ph)—, HO₂CCH(isopropyl)NHCOCH(methyl)CH₂N(CH₂Thy)-, etc.

The linkers may be any component capable of being selectively cleaved to release both T and II from the solid support. See, e.g., Greene and Wuts, "Protective Groups in Organic Synthesis", 2nd ed., Wiley, 1991. Specific linkers L'are depicted in Table I (note that -L-=—C(O)L'— or —CH₂—C(O)L'—), which also shows cleavage reagents. In designing a synthetic scheme, L and L' are chosen such that they are orthogonally reactive, i.e., they must allow for removal of either T or II (where T=T'—OH) without removal of the other since simultaneous cleavage of both T and II from the solid support is disadvantageous. In the structures as shown, the left-hand bond is the point of attachment to the solid support (via —C(O)— for L'and —C(O)— or —CH₂C(O)— for L) and the right-hand bond is the point of attachment to either T or II.

The tags of this invention, T, are chemical entities which possess several properties: they must be detachable from the solid supports, preferably by photolysis or oxidation; they must be individually differentiable, and preferably separable; they must be stable under the synthetic conditions; they must be capable of being detected at very low concentrations, e.g., 10⁻¹⁸ to 10⁻⁹ mole; they should be identifiable with readily-available equipment which does not require sophisticated technical capabilities to operate; and they should be relatively economical. The tags may be structurally related or unrelated, e.g., a homologous series, repetitive functional groups, related members of the Periodic Chart, different isotopes, combinations thereof, and the like. At the end of the combinatorial synthesis, to each solid support, there will usually be attached at least 0.01 femtomol, usually 0.001-50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, oxy, carboxy, amino, halo, or the like; isotopes; etc.

The materials upon which the combinatorial syntheses of the invention are performed are referred to as solid supports, beads, and resins. These terms are intended to include:

a) beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and b) soluble supports such as low molecular weight non-cross-linked polystyrene.

TABLE 1

LINKER GROUPS

| Linker Group, —L'— | Cleavage |
|---|---|
| 1. 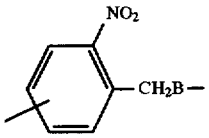 | hv |
| or 2. 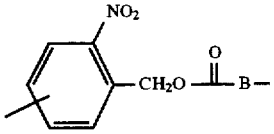 | hv |
| 3. 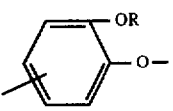 | Ce(NH₄)₂(NO₃)₆ |
| 4. RO— | Ce(NH₄)₂(NO₃)₆ |
| 5. —CH=CH(CH₂)₂— | O₃, OsO₄/IO₄—, or KMnO₄ |
| 6. —CH=CHCH₂— | O₃, OsO₄/IO₄—, or KMnO₄ |
| 7. —CH₂CH=CH— | O₃, OsO₄/IO₄—, or KMnO₄ |
| 8. 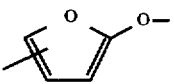 | 1) O₂ or Br₂, MeOH  2) H₃O⁺ |
| 9. —CH=CHCH₂O— | (Ph₃P)₃RhCl(H) |
| 10. 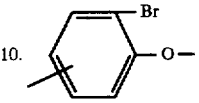 | Li, Mg, or BuLi |
| 11. —S—CH₂—O— | Hg⁺² |
| 12. 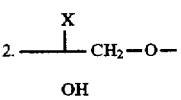 | Zn or Mg |
| 13. 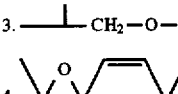 | Oxidation, e.g., Pb(OAc)₄ or H₅IO₆ |
| 14. 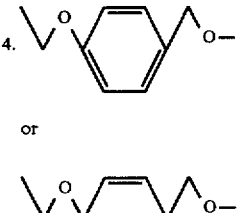 | H₃O⁺ |
| or 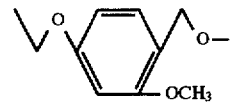 | |

R= H or lower alkyl;
B= O or NH; and
X= electron withdrawing group such as Br, Cl, and I.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D and L), isomers may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

Utility

The library of the present invention is useful as a screening tool for discovering new lead structures by evaluation across an array of biological assays, including the discovery of selective inhibition patterns across isozymes. The library is thus a tool for drug discovery; i.e., as a means to discover novel lead compounds by screening the library against a variety of biological targets and to develop structure-activity relationships (SAR) in large families of related compounds. The library may be tested with the ligands attached to the solid supports as depicted in Formula I or I', or the compounds II may be detached prior to evaluation. With the compounds of Formula I or I', screening assays such as FACS sorting and cell lawn assays may be used. When a compound is detached prior to evaluation, its relationship to its solid support is maintained, for example, by location within the grid of a standard 96-well plate or by location of activity on a lawn of cells. Whether the compounds are tested attached or detached from the solid supports, the tags attached to solid support associated with bioactivity may then be decoded to reveal the structural or synthetic history of the active compound (Ohlmeyer et al., *Proc. Natl. Acad. Sci. USA*, 90, 10922-10926, Dec. 1993 and Still et al., Complex Combinatorial Chemical Libraries Encoded with Tags, WO 94/08051) or, alternatively, the structures may be determined by deconvolution. The usefulness of such a library as a screening tool is demonstrated by Burbaum et al., *Proc. Natl. Acad. Sci. USA*, 92, 6027-6031, June 1995, who describe the assaying of encoded combinatorial libraries for, e.g., carbonic anhydrase inhibition. Even if no compounds are found to be active in a given screen, such lack of activity often provides useful SAR information.

Assays for Determining Biological Activity

Assays for evaluating the compounds of the present invention are well known in the art. Although one usually does not know a priori in which specific assays a particular compound or group of library compounds will have activity, a useful system for screening libraries of the format of that described in the present invention, to identify activities with respect to a wide variety of enzymes and molecular targets, is the so-called lawn assay.

In a lawn assay, a library of solid supports, preferably beads, is screened for the ability of compounds on the supports to affect the activity of an enzyme. Using the lawn assay, supports containing the active compounds are quickly and easily located merely by viewing zones of inhibition in a matrix. In one embodiment, the solid supports are contacted with a colloidal matrix, such as agarose. The compounds are linked to the supports by a cleavable linker and released, e.g., by exposure to light. As they slowly diffuse out of the solid supports, zones of high concentration of the compounds are created in the supports' immediate vicinity. The compounds contact enzyme contained in the matrix. Substrate is contacted with the matrix and reacts with the enzyme. Conversion of substrate to product is measured by monitoring a photometric change in the substrate, or in a coenzyme or cofactor involved in reaction. For example, the substrate can be fluorogenic, i.e., becoming fluorescent when converted to product. In this case, compounds that are active inhibitors of the enzyme reaction are detected as dark zones of inhibition. The less active, or inactive, compounds are contained in the lighter areas.

Using this assay, positive results from an assay of a combinatorial library can be detected very quickly. Furthermore, compound activity can be quantitated by e.g., comparing the sizes of zones of activity. Once zones of activity have been determined, the relevant supports at the center of the zones can be located and the active compounds on those supports identified. The lawn assay thus allows large libraries of compounds to be quickly and easily screened. Very little effort is required to array the solid supports or assay the compounds released from the supports.

In another embodiment, the lawn assay is used to determine compounds that bind to a target molecule, and thereby affect a detectable signal generated by a labeled ligand bound to the target molecule. This assay allows screening of compounds that, e.g., act as agonists or antagonists of a receptor, or that disrupt a protein:protein interaction. It also allows detection of binding to DNA, RNA, or complex carbohydrates. For example, neurokinin receptor binds to a 7-nitrobenz-2-oxa-1,3-diazol-4-yl (NBD)-labeled peptide ligand. The labeled ligand has the following formula: PhCO-2,4-diaminobutyric acid(gamma-NBD)-Ala-D-trp-Phe-D-pro-Pro-Nle-NH2. NBD is a fluorophore, and binding of the labeled ligand to the neurokinin receptor increases NBD's fluorescence. When a compound displaces the NBD-labeled ligand from the neurokinin receptor, fluorescence of the NBD fluorophore is reduced (G. Turcatti, H. Vogel, A. Chollet (1995) *Biochemistry* 34, 3972-3980). A library of solid supports can be screened for compounds that bind to neurokinin receptor in a colloidal matrix using this method. Active compounds are found in zones of decreased fluorescence. As another example, a radioligand (tritium or $^{125}$iodine-labeled) can be used to screen for compounds binding to a receptor with the lawn assay by using Scintillation Proximity Assay beads (SPA™, Amersham Corp.) or scintillant coated plates (Flashplates™, Dupont NEN Research Products). Receptor is bound to SPA™ beads or to a Flashplate™ surface and radiolabeled ligand in a colloidal matrix is allowed to interact with the receptor. This interaction brings the radiolabel in close proximity with the scintillant and results in a scintillation signal. The signal can be detected using x-ray film, or other commercially available film that is specifically designed to detect tritium dependent scintillations. Compounds released into the matrix from the solid supports that bind to receptor and displace the radioligand reduce the scintillation signal, i.e., result in a zone of reduced scintillation. The receptor used in the assay can be e.g., membrane-bound, tethered to a solid phase, or solubilized.

When using the assay to find compounds that affect enzyme activity, it is advantageous to employ a substrate or product of the enzymatic reaction that generates a detectable signal. The difference in signal between the substrate and product should be significant. It is particularly preferred to use a substrate which generates little or no signal, and which converts to a product which generates a strong signal. If the substrate produces detectable signal which cannot be distinguished from that of the product, it can create background noise, thereby reducing the overall sensitivity of the assay. For this reason, non-fluorescent substrates that convert to fluorescent products, i.e., fluorogenic substrates, are preferred. One well known fluorogenic substrate is fluorescein diacetate, which converts to fluorescein in the presence of an esterase, such as carbonic anhydrase. Other fluorogenic substrates include 7-amino-trifluoromethyl coumarin (AFC), 4-trifluoromethylumbelliferyl (HFC), 7-amino-4-methylcoumarin (AMC) and 4-methoxy-2-naphthylamine (MNA).

Alternately, a fluorescent substrate can be used that converts to a product having different excitation and emission characteristics. By using band-pass filters so that only the product is excited and detected, the substrate can be effectively screened out. An example of such a fluorescent substrate is peptidylaminomethylcoumarin, which is converted by an appropriate protease, such as thrombin, to free aminomethylcoumarin. The free aminomethylcoumarin excites and emits at different wavelengths than does the peptidyl-aminomethylcoumarin (S. Kawabata et al. (1988) *Eur. J. Biochem.* 172, 17).

It is also possible to use a substrate containing internally quenched fluorophores that become fluorescent when converted to product. Such quenching reactions are well known (E. Matayushi et al. *Science* 247, 954). For example, a peptide substrate can be produced having two fluorophores at opposite ends, one absorbing the fluorescence of the other. The substrate therefore emits a negligible amount of light. Upon cleavage of the peptide by a suitable protease, the absorbing fluorophore is released and no longer quenches the other fluorophore, resulting in an increase in fluorescence. One such substrate is 4(dimethylaminophenylazo)-benzoic acid (DABCYL)-Gabu-glu-arg-met-phe-leu-ser-phe-pro-5-[(2-aminoethyl)aminonaphthalene-1 sulfonic acid (EDANS), which when cleaved by an aspartyl protease (e.g., plasmepsin 11 of *Plasmodium falcioarum*) becomes fluorescent. In screening a library of aspartyl protease inhibitors using the lawn assay, those that are active inhibit cleavage of the substrate, allowing quenching to be maintained. Active compounds are found in dark zones of inhibition.

Fluorescence can be detected, e.g. using a field format fluorescence detection instrument, such as Fluorimager™ from Molecular Dynamics. This type of fluorimeter is capable of determining fluorescence over a large area. It is also possible to detect fluorescence using a CCD camera and to transfer the image data to a computer. The image can be generated by illumination of the fluorophore with light of the wavelength that specifically excites it. Detection can be optimized by using a bandpass filter between the camera and the assay that is specific for the emission wavelength of the fluorophore.

Assays that measure a change in fluorescence are preferred as they are believed to result in the greatest sensitivity. Any method, however, can be used that measures a change in signal from one of the compounds involved in the reaction as a result of conversion of the substrate to product, or displacement of the labeled ligand from the target. An example of an assay for compounds that affect a chromogenic substrate, p-nitrophenylphosphate, is described in the examples. It is also possible, for example, to measure a change in absorbance. For example, NADP is a common cofactor in many enzymatic reactions. Absorbance changes as NADPH is converted to NADP by, for example, neutrophil NADPH oxidase (such as during an oxidative burst associated with an immune response). This change can be monitored to determine zones of inhibition for compounds that inhibit this and other enzymes that use NADP, NADPH, NAD, and NADH as co-factors. The sensitivity of assays that measure a change in absorbance is believed to be generally lower than those that measure a change in fluorescence.

Other examples of detectable changes resulting from conversion of substrate to product include chemiluminescent changes and scintillation changes. Scintillation changes can be detected as described above for receptor binding with the exception that a substrate is attached to the scintillant (i.e., to the bead or plate containing scintillant). For example, a radioactive reagent, such as tritiated farnesyl pyrophosphate, can be added to the substrate by an enzyme such as farnesyl protein transferase. Transferase inhibitors prevent addition of the tritiated farnesyl pyrophosphate to the substrate, resulting in a reduction in detectable scintillations; i.e., transferase inhibitors are found in zones of reduced scintillation. In an alternative assay, removal of the radioactive portion of a substrate attached to the scintillant, such as by cleaving with a protease, releases the radiolabeled portion (i.e., moves it away from the scintillant). In such an assay, protease inhibitors cause an increase in scintillation, i.e., are found in zones of increased scintillation. As noted above, the scintillation signal can be detected using x-ray film, or film that is specifically designed to detect tritium dependent scintillations.

For assaying binding to a target molecule, a labeled ligand provides a signal that indicates such binding. The label is preferably a fluorescent moiety that alters its signal as a result of target molecule binding. Examples of such fluorescent moieties are NBD and 5-(dimethylamino)-1-naphthalenesulfonyl (Dansyl) chloride.

Colloidal matrices that are useful for the lawn assay include silica gel, agar, agarose, pectin, polyacrylamide, gelatin, starch, gellan gum, cross-linked dextrans (such as Sephadex™) and any other matrix that allows diffusion of compound from the solid supports in a limited region. Low melting-temperature agarose is preferred, generally in an amount of 0.5–2.0%, wt./vol. The colloidal matrix can be chosen to obtain a desired rate of diffusion. It is generally preferred to use a matrix that allows a high concentration of compounds to be easily obtained.

In carrying out the assay to determine compounds that affect enzyme activity, the solid supports are preferably embedded in a matrix containing the relevant enzyme. Following cleavage, compound diffuses from the support into the matrix and contacts the enzyme. Substrate is then added and, as it diffuses into the colloidal matrix, active compounds inhibit conversion to product. By following such a procedure, compounds to be screened are allowed to interact with enzyme before the enzyme contacts substrate. This is believed to be advantageous because it allows compounds the best opportunity to inhibit the enzyme, and thus results in the clearest zone of inhibition.

It is also possible, however, to embed the solid supports in a matrix that contains dispersed substrate. Following cleavage, the matrix can be contacted with enzyme. This procedure is not believed to be as sensitive since the compounds may not efficiently bind to the enzyme.

Solid supports can also be applied to the matrix's surface and the compounds allowed to diffuse into the matrix. This can be done, for example, by arraying the solid supports on the surface of a stretched sheet of plastic film (e.g., Parafilm™), and then applying the sheet to the surface of the matrix.

In assaying for compounds that affect enzyme activity, it may be desirable to use two colloidal matrices. For example, one matrix can contain enzyme and beads and the other can contain substrate. Contacting the surfaces of the matrices with each other allows the substrate to come into contact with the enzyme. It is also possible to add a solution of substrate over the surface of a matrix containing enzyme and embedded supports. Adding solution is preferred when, e.g., the substrate interferes with detection. Solution containing the substrate can be removed prior to determining the zones of activity.

When using the lawn assay to screen for binding to a target molecule, there is generally no need for more than one matrix. A matrix contains the target molecule bound to the labeled ligand which emits a detectable signal indicating binding to the target molecule. Compounds from the solid supports are diffused into the matrix, preferably from embedded supports using photolysis. Alternatively, however, labeled ligand can be diffused into the matrix from a second matrix (or liquid layer) after release of the compounds in the matrix. This allows the compounds to contact the receptor before interaction with the labeled ligand, which can be advantageous.

Compounds can be cleaved from the solid supports either before or after the supports are contacted with the colloidal matrix. For example, solid supports may contain acid cleavable linkers, as further described below. These linkers can be cleaved in a gaseous acidic atmosphere before placing the support on the matrix. The compounds, although cleaved, remain on the surface of the supports and diffuse into the matrix when the supports are placed on it. It is even possible to cleave the compounds prior to pouring low-melt liquid agarose over the solid supports. While some of the compounds will be washed away, sufficient compound can remain on the support's surface to result in a recognizable zone of activity.

Where the compounds are cleaved after the beads are embedded in the colloidal matrix, it is preferred to use photolysis, e.g., cleaving by exposure to UV light. By adjusting light exposure, it is possible to control the amount of compound that diffuses into the matrix. If more light is applied, by increasing intensity or duration, more cleavage results, in turn releasing more compound into the matrix. This allows the amount of active compound released to be adjusted, so that zones of activity are only produced for compounds that are most active. The amount of compound released can also be optimized to produce zones that are most distinct.

The solid supports can be in a random arrangement, or in an ordered one. Preparing a random arrangement of solid supports requires little effort. For example, a library of beads can be suspended in a solvent, such as ethanol, and deposited on the bottom of a Petri plate. After the solvent has completely evaporated, a layer of agarose containing the relevant enzyme or target molecule can be poured over the beads. Alternatively, an ordered array can be used to space beads apart and allow easier identification of those that are active. In one example of an ordered array, beads are arrayed on a rigid template, such as a thin glass disk having tapered holes. The tapered holes are sized to allow only single beads to settle into them. Beads are suspended in a solvent, such as ethanol, and washed over the top of the template to fill each hole with one bead. The beads can then be cleaved in the dry state, and the template set down on the colloidal matrix. Capillary action wets the beads, facilitating diffusion of the cleaved compounds into the matrix. Zones of activity can be observed immediately below beads containing active compounds. It is possible to remove the template prior to detecting zones of activity if an image of the template on the matrix is made. This image can later be used to correlate the zones of inhibition in the matrix with the positions of beads on the template.

Ordered arrays also may be useful in identifying the compounds on supports that are associated with zones of activity. Specifically, the array can be ordered so that the position of the solid support on the array corresponds to the identity of the compound. Thus, once an assay has been carried out, and the position on the array determined for a support carrying an active compound, the identity of that compound can be easily determined.

Preferably, however, the identity of active compounds is determined using the encoding system described above, which employs tags T encoding the identity of the compounds are applied to the solid supports.

The assay is preferably carried out so that there is slow diffusion of the compound from the solid support following cleavage. This results in a high concentration of compound in the vicinity of the bead. Thus very little compound is required to cause a distinct zone of activity. Most of the compound remains on the support for any subsequent assays that are required. Such further assays may be needed if more than one solid support is found in the zone of activity. It may then be necessary to retest the supports from the zone to determine which releases the active compound. Reassaying may be required as a matter of course if many thousands of beads are screened at high density. Reassaying may also be desirable to test for selectivity, i.e. to determine which active compounds are inactive in a second assay that tests for a different property.

With combinatorial libraries containing thousands of related compounds, many compounds may be found that have some degree of activity. It therefore may be to useful to use the lawn assay to distinguish the most potent compounds. In the assay, if the amount of compound released from each support is approximately the same, potent compounds have a detectable effect further from the bead than weak compounds do, at any given time. Thus, the more active compounds create a larger zone of activity. Furthermore, the zone of activity of the most active compounds lasts longer. Thus, it is possible to quantitate the activity of the compound eluted from the solid support by the size of the zone of activity, as well as by the duration of the zone following cleavage.

Reducing photolysis time reduces the amount of compound released from the support. As the concentration of the compounds is lowered, those that are less active become more difficult to detect. As a result, the number of active compounds drops. In general it is found that compounds that are detectable at the shortest elution times, i.e., that are most potent, are also identified as most potent using conventional solution-phase screening. The activity of the inhibitors is found to correlate with the size and duration of the zone of activity: the most potent compounds produce the largest zones for the longest time, for any given amount of photolysis.

When assaying a library containing many active compounds, it may be desirable to screen using a low density of solid supports, i.e., a low number of supports per $cm^3$ of matrix. While requiring more assays to screen the entire library, it is less likely that supports will have to be retested to determine which contains the active compound. Screening a large library containing many active members at a low density is often more efficient than screening at high density, since rescreening supports is time consuming. The optimum density for screening can be determined for a given library by comparing the throughput in the initial assay with the effort required to re test active supports. Other factors which affect optimum screening density include the cost of the target and the size of the library.

When several large libraries are available for testing, it may be advantageous to incompletely evaluate each library by "scouting" each at high density for active compounds. Screening at high density allows one to statistically evaluate the number and potency of active compounds in each library. Libraries which contain the most active compounds can be more thoroughly tested.

If the proportion of active compounds screened in the assay is high, a second assay of the active compounds may be performed to choose those that should be further evaluated. The second assay can determine whether there is cross reactivity with other targets, i.e., a "selectivity screening". For example, a given library of compounds can be screened for activity against HIV protease, a member of the aspartyl protease family, using DABCYL-gAbu-Ser-Gln-Asn-Tyr-Pro-Ile-Val-Gln-EDANS. Compounds found active in the initial assay can be counterscreened against a second, different aspartyl protease, such as cathepsin D. Alternately, all compounds screened in the assay for activity against HIV protease could be simultaneously screened in the counter assay.

It is also possible to test for compounds that interfere with proteins that inhibit enzyme activity. In such an assay, the most active compounds prevent enzyme inhibition, resulting in more enzymatic catalysis. Thus, when a fluorogenic substrate is used, active compounds result in a brighter zone of activity. For example, P16 is a known protein inhibitor of cyclin-dependent kinase-4 (Cdk-4). Using the lawn assay, Cdk-4, Cyclin D1, P16, a fluorogenic substrate and a library of beads to be screened can be included in a layer of low-melt agarose. Following photocleavage, and after allowing sufficient time to convert substrate to product, the gel can be subjected to an electrophoretic separation. Product migrates to the anode, where it is preferably trapped on an anode filter. The location of product on the filter indicates the position in the gel of compound that disrupts P16 inhibition of Cdk4.

In another embodiment of the lawn assay, an electrophoretic procedure is used to separate substrate from product to increase the sensitivity of the assay. In this embodiment, a substrate is used which changes charge when converted to product. An example of such a substrate is the peptide leu-arg-arg-ala-ser-leu-gly attached to a fluorophore, sold commercially as Pep-Tag™ (Promega Corp.). Protein kinase A (PKA) phosphorylates this substrate, which has net +1 charge, to form a phosphopeptide which has a net −1 charge. A lawn assay is performed in which PKA is contacted in a colloidal matrix with substrate and a library of potential inhibitors. An electrophoretic separation is then carried out across the width of (i.e., perpendicular to) the matrix. The phosphopeptide (i.e., product) moves towards the anode, and the dephosphopeptide (i.e., substrate) moves towards the cathode. If a membrane is applied to one or both sides of the matrix during electrotransfer, electroblotting can be achieved. For example, the phosphopeptide can be electroblotted to a suitable membrane, such as an Immobilon™ CD membrane. Alternately, the dephosphopeptide can be electrotransferred to an appropriate paper, such as Whatman™ 3 MM paper. In another embodiment, the substrate and product can be chosen so that one is neutral and one is charged. Application of the electrophoretic field will remove the charged moiety. The resulting matrix will contain only the neutral moiety, thereby allowing detection of compounds that affect the conversion to product. The position of the bead containing the active compound can be determined by fluorescent imaging of the substrate or product, using, e.g., photography or video imaging. This technique increases sensitivity of the lawn assay by separating fluorescent substrate from fluorescent product, concentrating the fluorescent image, and by eliminating compounds from the matrix that might cause background signal. Other protein kinases and phosphatases such as protein kinase C, cyclin dependent kinases, MAP kinases, and inositol monophosphatase can also be used with appropriate substrates in this method. A protease can also be screened by this method by using a substrate consisting of an appropriate peptide linked to a labeling moiety, such as a fluorophore. The peptide sequence is chosen so that the substrate and product will migrate differentially in an electric field.

Enzymes that can be used in the assay include, but are not limited to, the following:

Acid Phosphatase
Activated Protein C
Alkaline Phosphatase
Aminopeptidases B & M
Amyloid A4-Generating Enzyme
Angiotensinase
Aryl Sulfatase
β-Galactosidase
β-Glucosidase
β-Glucuronidase
Calpains I & II
Cathepsins B, C, D, & G
Cholinesterase
Chymotrypsin
Collagenase
Dipeptidyl Peptidases I–IV
Elastase
Endothelin Converting Enzyme
Factor Xa
Factor XIa
Factor XIIa Df-Protease
Furin
γ-Glutamyltranspeptidase
Granzymes A & B
HIV Protease
IL-1B Convertase
Kallikrein
Lysozyme
Mast Cell Protease
Peroxidase
Plasmin
Prohormone Convertase
Γ ANP Precursor Processing Enzyme
Renin
Spleen Fibrinolytic Proteinase
Staphylocoagulase
Thrombin
Tissue Plasminogen Activator
Trypsin
Tryptase
Urokinase The assay procedure is further illustrated by the Examples below.

Examples of the Use of the Assay

The lawn assay is performed in Petri plates using two layers of agarose, each about 1.5 mm thick. The first layer contains TentaGel S—NH$_2$™ beads and enzyme. The TentaGel S—NH$_2$™ beads have compounds to be screened attached thereto by a photocleavable linker and chemical tags attached for identifying the compounds, prepared according to methods described herein. The beads are either placed on the Petri plate and agarose poured over them, or beads and agarose are first mixed and then poured together onto the plate. A second layer of agarose containing the fluorescein diacetate is contacted with the first layer to initiate the reaction.

More specifically: 50 mM sodium phosphate, pH 7.4, is used as a buffer and all solutions equilibrated in a 370° C. water bath immediately prior to initiation of the assay. 0.1 mL of 5.3 µM bovine carbonic anhydrase (Sigma Chemical Co.) is diluted in 2.15 mL of buffer, and 1.25 mL of 2.5% low-gelling agarose added (SeaPlaque™, FMC BioProducts). Library beads suspended in methanol are added to a 6 cm polystyrene petri plate and, if necessary, distributed with a flat pipette tip. After evaporation of the methanol, the agarose solution is poured over the beads and allowed to gel at room temperature for 2–3 minutes. (Alternatively, dry beads can be added to a mixing tube, and then enzyme and agarose added; the mixture is then vortexed and poured.) The plate is then placed under a long wave (360 nm) UV lamp (Blackray™ UVP, Inc.) for from 5 sec to 1 hour. After irradiation, 0.01 mL of fluorescein diacetate (10 mM in DMF, Molecular Probes, Eugene, Oreg.) is combined with 2.25 mL buffer and 1.25 mL of 2.5% agarose and poured over the first agarose layer. Detection is achieved by illumination using a short wavelength UV lamp (UVX, 254 nm) and image capture using a CCD camera coupled to a computer with NIH Image software obtained from the National Institutes of Health.

Fluorescein diacetate is hydrolyzed to produce fluorescein as the reaction proceeds. The plate then becomes significantly brighter except in the vicinity of beads that release inhibitors, thereby forming zones of inhibition. Beads at the center of these zones are removed with a hollow glass tube, or a spatula, and washed in methanol/methylene chloride (1:1), or with hot water (800° C.), to remove most of the agarose. After a final rinse in methanol, beads are either retested in a separate assay using the methods described above to confirm activity, or analyzed to determine the relevant compound structures by tag decoding.

EXAMPLE 1
Assay of Two Known Inhibitors

In this example, two compounds were tested for inhibition of carbonic anhydrase by the lawn assay. Carbonic anhydrase inhibitors are useful in treating e.g., glaucoma. Results were compared with those obtained using a conventional solution phase assay.

It is known that there is a high correlation between compounds that inhibit binding of dansylamide to carbonic anhydrase and those that inhibit conversion of fluorescein diacetate to fluorescein by carbonic anhydrase. This is believed to result from dansylamide and fluorescein diacetate occupying the same active site (a zinc atom) on carbonic anhydrase. The solution phase assay measured inhibition of dansylamide binding. The lawn assay measured inhibition of the conversion of fluorescein diacetate to fluorescein.

Two aryl sulfonamide-containing compounds (compounds "I" and "II") were synthesized on TentaGel® beads (Rapp Polymere) and assayed in the standard solution-phase assay and in the lawn assay. Compounds containing aryl sulfonamide substituents are known to be potent inhibitors of carbonic anhydrase. In the solution phase assay, Ki's were determined to be 4 and 660 nM for compounds I and II respectively.

In the lawn assay, beads containing each compound were embedded in agarose in a series of petri plates. The right side of each plate contained beads with compound I, and the left side contained beads with compound II. Separate plates were irradiated for 2.5, 5, 10, 20 and 30 minutes. The more potent inhibitor of carbonic anhydrase (compound I) showed a clear zone of inhibition after only 2.5 minutes of photolysis. The weaker inhibitor (compound II) caused only a weak zone of inhibition after five minutes of photolysis. Ten minutes of photolysis was required to obtain a distinct zone. The clearest zones of inhibition were observed at the shortest time after photolysis. Zones at five minutes after photolysis were all sharper than at 15 minutes after photolysis. At 30 minutes after photolysis, all zones were much less distinct; some zones (for compound II) had disappeared.

In a second experiment, a plate containing beads with compounds I and II was irradiated for a predetermined period of time. The size and duration of the resulting zones of inhibition were determined. The zones resulting from compound I were larger than those resulting from compound II. Furthermore, the zones for compound I could be observed for a longer time: signal from compound I persisted for more than two hours (although the zones became very diffuse) while signal for compound II all but disappeared after 90 minutes. In addition, zones of inhibition for compound I were more distinct, i.e., there was greater contrast between the zones and the surrounding areas.

EXAMPLE 2
Lawn Assay for Inhibitors of Inositol Monophosphate

An assay for inhibitors of inositol monophosphate is carried out in the same manner as described above for carbonic anhydrase inhibitors, with the following substitutions: The buffer used is 20 mM Tris, 1 mM EGTA, pH 7.8. The agarose layer contains 1 mg/mL of recombinant human inositol monophosphate, purified from $E.\ coli$, and 10 mM $MgCl_2$. The substrate is methylumbelliferyl phosphate (Sigma Chemical Company, St. Louis Mo., M-8883), CSPD (Tropix, Bedford Mass.) or CDP-Star (Tropix). CSPD and CDP-Star are chemiluminescent substrates. The preferred substrate is CSPD. Inositol monophosphate is believed to be the molecular target of lithium therapy in bipolar disease.

EXAMPLE 3
Lawn Assay for Compounds that Affect Tyrosine Phosphatase

This test chromogenically assays compounds for their affect on the catalytic domain of human SHPTP1, a protein tyrosine phosphatase [Pei et al. (1993) PNAS 90, 1092] using p-nitrophenylphosphate as a substrate. This enzyme is assayed as described above for carbonic anhydrase, with the following substitutions. The buffer used is 100 mM N,N-bis(2-hydroxyethyl)glycine, pH 8. The first (lower) agarose layer contains 0.5 mg/mL recombinant human SHPTP1 catalytic domain, purified from $E.Coli$, and the substrate is 4-nitrophenyl phosphate (Sigma Chemical Corp.). Enzyme activity corresponds with the release of the 4-nitrophenolate anion ($\lambda_{max}$ 400 nm, $\epsilon$ 18,300 $M^{-1}\ cm^{-1}$), which appears as a yellow color on a clear background. Areas where affecters of the SHPTP1 catalytic domain are found are distinguished by either clear zones of inhibition or more colored zones of stimulation.

Methods of Synthesis

The compounds of the present invention can be prepared according to the following methods. At each step in the synthesis each solid support upon which a compound is being synthesized is uniquely tagged to define the particular chemical event(s) occurring during that step. The tagging is accomplished using identifiers such as those of Formula IV, which record the sequential events to which the support is exposed during the synthesis, thus providing a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis with a combination of identifiers which uniquely define the chosen variables such as reactant, reagent, reaction conditions, or combinations of these, one can use the identifiers to define the reaction history of each solid support.

In carrying out the syntheses, one begins with at least $10^4$, desirably at least $10^7$, and generally not exceeding $10^{15}$ solid supports. Depending on the pre-determined number of $Aa^1$ choices for the first step, one divides the supports accordingly into as many containers. The appropriate reagents and reaction conditions are applied to each container and the combination of identifiers which encode for each $Aa_1$ choice is added and attached. Depending on the chemistries involved, the tagging may be done prior to, concomitantly with, or after the reactions which comprise each choice. As a control, sample supports may be picked at any stage and a portion of their tags detached and decoded to verify that the correct tags are bound to the sample supports. As needed, one may wash the beads free of any excess reagents or by-products before proceeding. At the end of each step, the supports are combined, mixed, and again divided, this time into as many containers as pre-determined for the number of $Aa^2$ choices for the second step in the synthesis. This procedure of dividing, reacting, tagging, and remixing is repeated until the combinatorial synthesis is completed.

Scheme 1

A batch of amino-functionalized PEG-grafted polystyrene beads derivatized with the acid cleavable PHB linker (PHB resin) is equally divided into a pre-determined number of reaction vessels and reacted with either an N-Fmoc protected primary or secondary amino acid (e.g., see Table 1-1) to generate 1a or 1b. The resin is divided into equal batches for separate coupling of each amino acid through ester bond formation. After coupling, a small portion of each batch of resin may be removed and the ligand cleaved in TFA:$CH_2Cl_2$ (7:3) as a quality control for the reaction in this combinatorial step.

Unique tagging of the supports in each reaction vessel is achieved with combinations of identifiers encoded in a binary scheme, e.g., as depicted in Table 1-1 for seven choices of $Aa^1$. The identifiers are attached by adding a solution of up to two identifiers in DCM (in a 7.5–15% wt./wt. identifier:solid support ratio, depending on the signal strength of the identifier) to a batch of supports suspended in ethylacetate or $CH_2Cl_2$ and shaking the mixture for 0.5–1 hr. A dilute solution of rhodium trifluoroacetate dimer is added and the mixture is immediately shaken overnight, then washed in $CH_2Cl_2$. The procedure is repeated as necessary to add additional identifiers. For purposes of simplicity the identifiers are not shown in the schematics.

Scheme 2

The compounds 1a and 1b are pooled, mixed, and divided into a pre-determined number of reaction vessels. The mixtures of Compounds 1a and 1b are then treated with piperidine/DMF to de-protect the amino group of the ligand element $Aa^1$. Each vessel is then treated with one amino acid reagent (e.g., see Table 1-2) corresponding to ligand element $Aa^2$ for separate coupling of each amino acid by amide bond formation to produce 3.

Unique tagging of the supports in each reaction vessel is achieved with combinations of additional identifiers encoded in a binary scheme, e.g., as depicted in Table 1-2 for 15 choices of $Aa^2$. The identifiers are attached by adding a solution of up to two identifiers in DCM (in a 7.5–15% wt./wt. identifier:solid support ratio, depending on the signal strength of the identifier) to a batch of supports suspended in ethylacetate or $CH_2Cl_2$ and shaking the mixture for 0.5–1 hr. A dilute solution of rhodium trifluoroacetate dimer is added and the mixture is immediately shaken overnight, then washed in $CH_2Cl_2$. The procedure is repeated as necessary to add additional identifiers.

Scheme 3

Compounds 3 are pooled, mixed, and divided into a pre-determined number of reaction vessels. The mixtures of compounds 3 are then treated with piperidine/DMF to de-protect the amino group of the ligand element $Aa^2$. Each vessel is then treated with one aromatic or heteroaromatic carboxaldehydes reagent (e.g., see Table 1-3) corresponding to ligand element $CH_2Ar^1$ dissolved in toluene for separate two step reductive amination. The resin is agitated for 16 hr, filtered, and washed. The imine thus produced is re-suspended in methanol and a solution of sodium cyanoborohydride, and agitated to reduce the imine and produce 4.

Unique tagging of the supports in each reaction vessel is achieved with combinations of additional identifiers encoded in a binary scheme, e.g., as depicted in Table 1-3 for 31 choices of $Ar^1$. The identifiers are attached by adding a solution of up to two identifiers in DCM (in a 7.5–15% wt./wt. identifier:solid support ratio, depending on the signal strength of the identifier) to a batch of supports suspended in ethylacetate or $CH_2Cl_2$ and shaking the mixture for 0.5–1 hr. A dilute solution of rhodium trifluoroacetate dimer is added and the mixture is immediately shaken overnight, then washed in $CH_2Cl_2$. The procedure is repeated as necessary to add additional identifiers.

Scheme 4

The tagged resin 4 are pooled, mixed, and divided into a pre-determined number of reaction vessels, each of which is agitated with one epoxide reagent dissolved in isopropanol (e.g., see Table 1-4), producing resin 5. The resultant resin batches may be either tagged as described above or retained separately as sub-libraries. Resin 5 may be cleaved in TFA:$CH_2Cl_2$ (7:3) to produce hydroxypropylamine II.

Scheme 5

TentaGel resin may be modified with bis-Boc Lysine 6 to increase the available reaction sites for ligand attachment. Bis-Boc-lysine 6 is coupled with aminofunctionalized TentaGel by amide bond formation. Coupling is achieved by shaking the resin, bis-Boc Lysine 6, DIC, and 4-DMAP in DCM at 25° C. for 16 hr to give 7. The resin 7 is then washed alternately with methanol and DCM and then dried under vacuum. To deprotect the resin, a 30% TFA solution in DCM (100 mL) is added. The vessel is shaken at 25° C. for 1 hr, at which time the resin is washed with DCM, then treated with a solution of 10% triethylamine in DCM, then washed with DCM and DMF to produce de-protected resin 8. To attach the linker, to the deprotected resin is added 4-acetoxymethylphenoxyacetic acid, DIC, and 4-DMAP in DCM at 25° C. for 16 hr. The resin is then washed alternately with methanol and DCM. The acetyl protecting group is removed by treatment (2×) of the resin with hydrazine in methanol (10% v/v) for 8 hr. The resulting lysine/linker-derivatized resin 9 is alternatively washed with methanol and DCM and then dried in vacuo.

For purposes of simplicity, the schemes do not show the use of this modification with lysine.

SCHEME 1
Ester Formation between PHB Resin and N-Fmoc Amino Acid (R)—OH* + HO—Aa¹HFmoc  →[DIC, 4-DMAP / 16.5 h, CH₂Cl₂, 25° C.]

1° amino acid (R)—O—Aa¹HFmoc   1a

(R)—OH + HO—Aa¹Fmoc  →[DIC, 4-DMAP / 16.5 h, CH₂Cl₂, 25° C.]

2° amino acid (R)—O—Aa¹Fmoc   1b where HO—Aa¹—H = Aa¹

*TentaGel—NH—C(=O)—CH₂—O—C₆H₄—CH₂OH = (R)—OH acid-cleavable PHB linker

SCHEME 2
ADDITION OF SECOND AMINO ACID

1a or 1b  →[i) 50% piperidine in DMF, 1 h, 25° C.; ii) HO—Aa²HFmoc, DIC, 4-DMAP, 14.5 h, CH₂Cl₂]

1° amino acid (R)—O—Aa¹-Aa²HFmoc   3 where HO—Aa²—H = Aa²

SCHEME 3
TWO-STEP REDUCTIVE AMINATION OF 1° AMINES WITH AROMATIC ALDEHYES (R)—O—Aa¹-Aa²HFmoc  →[i) 50% piperidine in DMF, 1 h, 25° C.; ii) 0.5M Ar₁CHO, toluene, 15 h, 25° C.; iii) 0.5M NaBH₃CN, MeOH, 4 h, 25° C.]

3

(R)—O—Aa¹-Aa²NH*—Ar¹   4

*N of Aa² is depicted to show the point of attachment

SCHEME 4
EPOXIDE OPENING (R)—O—Aa¹—Aa²NH*—Ar¹  +  ¹RX-CH₂-CH(O)CH₂ (epoxide)  →[i-PrOH, 48 h, 50° C.]

4

(R)—O—Aa¹-Aa²N(CH₂CH(OH)CH₂XR¹)(Ar¹)   5 (I)

→[TFA:CH₂Cl₂]

HO—Aa¹—Aa²N(CH₂CH(OH)CH₂XR¹)(Ar¹)   II

*N of Aa² is depicted to show the point of attachment

SCHEME 5
BIS-LINKER ATTACHMENT (R)—NH₂ + HO₂C-CH(NHBoc)-(CH₂)₄-NHBoc  →[DIC, 4-DMAP, DCM]

6

(R)—NH-C(=O)-CH(NHBoc)-(CH₂)₄-NHBoc  →[30% TFA, DCM]

7

(R)—NH-C(=O)-CH(NH₂)-(CH₂)₄-NH₂  →[1. HO₂C-CH₂-O-C₆H₄-CH₂OAc, DIC, 4-DMAP, DCM;  2. H₂NNH₂, MeOH]

8

(R)—NH-C(=O)-CH(NHC(=O)CH₂-O-C₆H₄-CH₂OH)-(CH₂)₄-NHC(=O)CH₂-O-C₆H₄-CH₂OH   9

The invention is further defined by reference to the following examples, which are intended to be illustrative and not limiting.

PREPARATION 1

IDENTIFIERS

Twelve compounds of the general formula:

$$\text{N}_2\text{=CH-C(=O)-C}_6\text{H}_3(\text{OCH}_3)\text{-O-(CH}_2)_n\text{-O-Ar}$$   IV wherein:
n=3–12 and Ar is pentachlorophenyl or
n=54–6 and Ar is 2,4,6-trichlorophenyl
were prepared according to Scheme 6 and the following illustrative example.

a) Methyl vanillate (0.729 g, 4.0 mmole), 1-hydroxy-9-(2,3,4,5,6-pentachlorophenoxy)nonane (1.634 g, 4.0 mmole) and triphenylphosphine (1.258 g. 4.8 mmole) were dissolved in 20 mL dry toluene under argon. DEAD (0.76 mL. 0.836 g. 4.8 mmole) was added dropwise and the mixture was stirred at 25° C. for one hr. The solution was concentrated to half volume and purified by flash chromatography eluting with DMC to give 1.0 g (1.7 mmole. 43%) of the product as a white crystalline solid.

b) The methyl ester from Step (a) (1.0 g. 1.7 mmole) was dissolved in 50 mL THF. 2 mL water was added. followed by LiOH (1.2 g. 50 mmole). The mixture was stirred at 25° C. for one hr. then refluxed for 5 hr. After cooling to 25° C.. the mixture was poured onto ethyl acetate (200 mL) and the solution was washed with 1M HCl (3×50 mL) then sat'd aq. NaCl (1×50 mL) and dried over sodium sulfate. The solvent was removed and the crude acid azeotroped once with toluene.

c) The crude material from Step (b) was dissolved in 100 mL toluene. 10 mL (1.63 g. 14 mmole) thionyl chloride was added. and the mixture was refluxed for 90 min. The volume of the solution was reduced to approx. 30 mL by distillation. then the remaining toluene was removed by evaporation. The crude acid chloride was dissolved in 20 mL dry DCM and cooled to −70° C. under argon and a solution of approx. 10 mmole diazomethane in 50 mL anhydrous ether was added. The mixture was warmed to r.t. and stirred for 90 min. Argon was bubbled through the solution for 10 min.. then the solvents were removed by evaporation and the crude material was purified by flash chromatography. eluting with 10–20% ethyl acetate in hexane. The diazoketone (0.85 g. 1.4 mmole. 82% yield over three steps) was obtained as a pale yellow solid.

An improvement was made to the final diazomethylation step. whereby the acid chloride was reacted with (trimethylsilyl)diazomethane and triethylamine to give the identifier. which was then used without further purification. This was a significant improvement over the original reaction with diazomethane. as the identifier was now obtained in high yield with no chlorometylketone byproduct. Also. purification by flash chromatography was no longer necessary. which in some cases had resulted in significant acid-catalyzed decomposition of the identifier.

Alternate Step c) To a solution of the acyl chloride (3.8 mmol. 1.00 eq.) and 1.85 mL (13.3 mmol. 3.50 eq.) of triethylamine in anhydrous THF/acetonitrile (1:1) at 0° C. under argon was added 5.7 mL (1 1.4 mmol. 3.00 eq.) of a 2.0M solution of (trimethylsilyl)diazomethane in hexanes. The resulting orange solution was stirred at 0° C. for 2 hr. then at 25° C. for 17 hr. (If a precipitate formed immediately upon addition of (trimethylsilyl)diazomethane. $CH_2Cl_2$ was added until the precipitate redissolved). EtOAc was added (250 mL). and the organic layer washed with saturated aq. $NaHCO_3$ (100 mL) and $H_2O$ (100 mL). then dried (anhydrous $MgSO_4$). Removal of the volatiles in vacuo gave the product as yellow crystals in 60–100% yield.

The other 11 identifiers of Formula IV were prepared by analogous synthetic routes. steps (a). (b). and (c).

In the synthesis of Example 1. the 12 identifiers were used to encode the combinatorial library. In Step 1. pentachlorophenyl identifiers where n=10-12 (abbreviated $C_{10}Cl_5$. $C_{11}Cl_5$. and $C_{12}Cl_5$) were used in the following binary encoding scheme: 001=(n=12). 010=(n=11) and 100=(n=10). In Step 2. pentachlorophenyl identifiers where n=6-9 (abbreviated $C_6Cl_5$. $C_7Cl_5$. $C_8Cl_5$. and $C_9Cl_5$) were used and encoded as follows: 0001=(n=9). 0010=(n=8). 0100=(n=7). and 1000=(n=6). In Step 3. pentachlorophenyl identifiers where n=3-5 (abbreviated $C_3Cl_5$. $C_4Cl_5$. and $C_5Cl_5$) were used and encoded as follows: 00001=(n=5). 00010=(n=4). and 00100=(n=3). Also in Step 3. trichlorophenyl identifiers where n=5-6 (abbreviated $C_5Cl_3$. and $C_6Cl_3$) were used and encoded as follows: 01000=(n=6). and 10000=(n=5).

Thus. in Step 1 reagent 3 (Table 1-1) is encoded "011" which represents tagging this choice in the synthesis with the two pentachloro-phenyl identifiers where n=11 and 12. Likewise. in Step 3 reagent 52 (Table 1-3) is encoded "01110" which represents tagging this choice in the synthesis with the pentachlorophenyl identifiers where n=4 and 3 and the trichlorophenyl identifier where n=6.

SCHEME 6
INDENTIFIERS

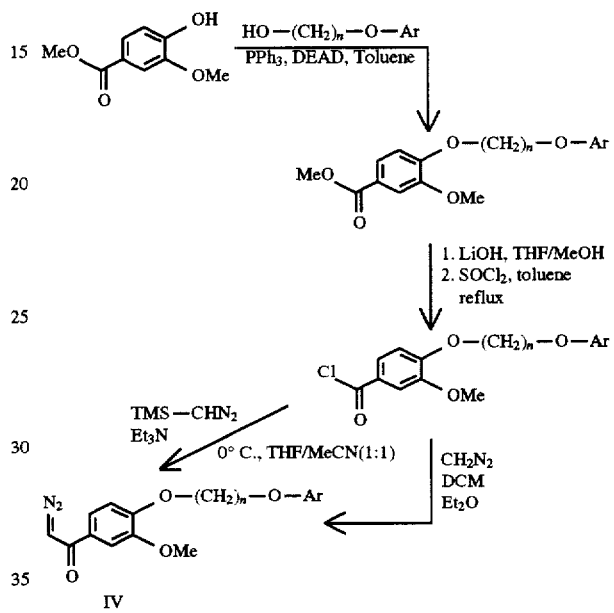

EXAMPLE 1

100.905 COMPOUND LIBRARY

Step 1
Ester Bond Formation

N-Fmoc-isonipecotic acid (3.66 g. 10.0 mmol. 5.00 eq) and 4-N,N'-dimethylaminopyridine (0.127 g. 0.500 mmol. 0.500 eq) were dissolved in 100 mL of methylene chloride and this solution was added to TentaGel™ S PHB resin (8.0 g. 0.26 mmol/g. 2.1 mmol. 1.0 eq). After agitation for 5 min. DIC (1.63 mL. 1.30 g. 10.0 mmol. 5 eq) was added. and then the resin was agitated at 25° C. for a further 16 hr. The resin was subsequently filtered and washed with 125 mL portions of methylene chloride (4×). methanol (2×). methylene chloride (1×). methanol (1×). and methylene chloride (2×). then dried in vacuo. Six other ester linked resin batches were prepared in an analogous manner using the reagents in Table 1-1.

Reaction completion was verified for each vessel by taking an ~0.30 g portion of each resin batch and cleaving the attached ligand by stirring for 4 hr in TFA:methylene chloride (7:3). The resin was removed by filtering the suspension through glass wool. Volatiles were then removed from the filtrate in vacuo to give the product. The structures of the recovered N-Fmoc-protected amino acids were confirmed by H NMR and the yields based on gravimetric analysis were in the range of 82% to 100%.

Encoding of Step 1

For all the encoding steps. when the $C_xCl_5$-linker-diazoketone reagents (x=3-12) were utilized. an amount of reagent equal to 7.5% by mass of the resin to be encoded was used. For the $C_yCl_3$-linker-diazoketone reagents (y=3-6), an amount of reagent equal to 15% by mass of the resin to be encoded was used.

Each of the seven resin batches in Step 1 was encoded with one or more of the $C_{12}Cl_5$-, $C_{11}Cl5$-, and $C_{10}Cl_5$-linker-diazoketones to produce the appropriate binary code. Identifiers were incorporated one at a time until the required binary code was completed. For example, resin batch 3 (8.0 g) was suspended in 180 mL of ethyl acetate and a solution of 0.60 g of $C_{12}Cl_5$-linker-diazoketone dissolved in 5 mL methylene chloride was added. After agitation for 2 hr. rhodium trifluoroacetate dimer (10 mL of a 1.5 mg/mL solution in methylene chloride) was added and the resin agitated at 25° C. for a further 16 hr. The resin was then filtered and washed with 150 mL portions of methylene chloride (4×), methanol (2×), methylene chloride (4×) and ethyl acetate(1×). This resin batch was again suspended in 180 mL of ethyl acetate and a solution of 0.60 g of $C_{11}Cl_5$-linker-diazoketone dissolved in 5 mL methylene chloride was added. After agitation for 2 hr, rhodium trifluoroacetate dimer (10 mL of a 1.5 mg/mL solution in methylene chloride) was added and the resin was agitated at 25° C. for a further 16 hr. The resin was subsequently filtered and washed with 150 mL portions of methylene chloride (4×), methanol (2×), and methylene chloride (4×), then dried in vacuo.

After encoding, the seven resin batches were combined as a suspension in methylene chloride, mixed to homogeneity, filtered, then dried in vacuo.

Step 2

The mixed resin from Step 1 was divided into 15 equal batches of 3.7 g (~0.89 mmol, ~0.24 mmol/g, 1.0 eq).

Deprotection

For each batch, N-Fmoc protecting groups were removed by washing the resin once with DMF, filtering, then suspending in 50 mL of a 50% v/v solution of piperidine and DMF and agitating at 25° C. for 60 min. Deprotection was verified by taking small portions of resin from each vessel and obtaining positive results in both the Kaiser test for primary amines and the bromophenol blue test for all amines. The resin was then filtered and washed with 50 mL portions of DMF (5×), methylene chloride (2×), DMF (1×), and methylene chloride (3×). The resin was used directly in the next reaction without drying.

Amide Bond Formation

Each of the fifteen N-Fmoc amino acids in Table 1-2 (4.4 mmol, 5.0 eq), was separately dissolved in 50 mL of methylene chloride (up to 10 mL DMF was added for solubility, if needed) and 4-N,N'-dimethylaminopyridine (0.054 g, 0.44 mmol, 0.50 eq) was added. Each solution was added separately to one of the fifteen batches of resin (3.7 g, ~0.89 mmol, 1.0 eq) and the resin agitated for 5 min. DIC (0.56 g, 4.4 mmol, 5.0 eq) was then added to each vessel and the resin agitated at 25° C. for 15 hr. Reaction completion was verified for each vessel by taking small portions of resin and obtaining a negative result in the Kaiser test for primary amines and the bromophenol blue test for all amines. The resin was filtered and washed with 50 mL portions of methylene chloride (4×), methanol (2×), methylene chloride (1×), methanol (1×), and methylene chloride (2×), then dried in vacuo.

Encoding of Step 2

Each of the fifteen resin batches in Step 2 was encoded with one or more of the $C_9Cl_5$-, $C_8Cl_5$-, $C_7Cl_5$-, and $C_6Cl_5$-linker-diazoketones to produce the appropriate binary code. Identifiers were incorporated one at a time until the required binary code was completed. For example, resin batch 1 (3.7 g) was suspended in 60 mL ethyl acetate and a solution of 0.28 g of $C_9Cl_5$-linker-diazoketone dissolved in 1.7 mL methylene chloride was added. After agitation for 2 hr, rhodium trifluoroacetate dimer (3.33 mL of a 1.5 mg/mL solution in methylene chloride) was added and the resin agitated at 25° C. for a further 16 hr. The resin was subsequently filtered and washed with 50 mL portions of methylene chloride (4×), methanol (2×), and methylene chloride (4×), then dried in vacuo.

After encoding, the fifteen resin batches were combined as a suspension in methylene chloride, mixed to homogeneity, filtered, then dried in vacuo.

Step 3

The mixed resin from Step 2 was divided into thirty-one batches of 0.95 g (~0.22 mmol, ~0.23 mmol/g, 1.0 eq). The encoding of Step 3 was done prior to the third combinatorial step.

Encoding of Step 3

Each of the thirty-one resin batches in Step 3 was encoded with one or more of the $C_5Cl_5$-, $C_4Cl_5$-, $C_3Cl_5$-, $C_6Cl_3$- and $C_5Cl_3$-linker-diazoketones to produce the appropriate binary code. Identifiers were incorporated one at a time until the required binary code was completed. For example, resin batch 1 was suspended in 12 mL of ethyl acetate and a solution of 0.0714 g of $C_5Cl_5$-linker-diazoketone in 0.33 mL of methylene chloride was added. After agitation for 1 hr, rhodium trifluoroacetate dimer (0.67 mL of a 1.5 mg/mL solution in methylene chloride) was added and the resin agitated at 25° C. for a further 16 hr. The resin was subsequently filtered and washed with 15 mL portions of methylene chloride (4×), methanol (2×), and methylene chloride (4×), then dried in vacuo.

Deprotection

For each batch, N-Fmoc protecting groups were removed by washing the resin once with DMF, filtering, then suspending in 12 mL of a 50% v/v solution of piperidine and DMF and agitating at 250° C. for 60 min. Deprotection was verified by taking small portions of resin from each vessel and obtaining positive results in the Kaiser test for primary amines and the bromophenol blue test for all amines. The resin was then filtered and washed with 15 mL portions of DMF (5×), and methylene chloride (2×), DMF (1×), methylene chloride (3×). The resin was used directly in the next reaction without drying.

Two-Step Reductive Amination a) Imine formation

Each of the thirty-one aromatic and heteroaromatic carboxaldehydes in Table 1-3 (5.00 mmol, 22.8 eq) was separately dissolved in 10 mL toluene (up to 2 mL DMF was added for solubility, if needed) and separately added to one of the thirty-one batches of resin (0.95 g, ~0.22 mmol, 1.0 eq). The resin was then agitated at 25° C. for 16 hr. The resin was subsequently filtered and washed with 15 mL portions of toluene (2×), methylene chloride (2×), methanol (2×), methylene chloride (2×), and methanol (2×). The resin was used directly in the next reaction without drying.

b) Imine reduction

Each batch of resin (~0.22 mmol, 1.0 eq) from step a was suspended in 5 mL methanol and a solution of sodium cyanoborohydride (0.330 g, 5.00 mmol, 22.8 eq) in 5 mL methanol was added. The resin was then agitated at 25° C. for 4 hr. Reaction completion was verified for each vessel by taking small portions of resin and obtaining a negative result in the Kaiser test for primary amines and a positive result in the bromophenol blue test for all amines. The resin was subsequently filtered and washed with 15 mL portions of methanol (4×), methylene chloride (2×), methanol (2×), and methylene chloride (2×), then dried in vacuo.

After reaction completion, the thirty-one resin batches were combined as a suspension in methylene chloride, mixed to homogeneity, filtered, then dried in vacuo.

Step 4

Epoxide Opening

The mixed resin from Step 3 was divided into thirty-one equal batches of 0.87 g (~0.21 mmol, ~0.24 mmol/g, 1.0 eq). Each of the thirty-one epoxides in Table 1-4 (12 mmol) was separately dissolved in isopropanol (10 mL, with up to 2 mL DMF added for solubility, if needed) and separately added to one of the thirty-one batches of resin (0.87 g, 0.21 mmol, 1.0 eq). The resin was then agitated at 50° C. for 48 hr. The resin was subsequently filtered and washed with 15 mL portions of methanol (4×), methylene chloride (2×), methanol (2×), and methylene chloride (2×), then dried in vacuo. Each of these final resin batches was individually recovered and stored as a separate sub-library obviating any encoding for Step 4.

EXAMPLE 2

VERIFICATION OF SYNTHESIS

Two members of the library of the present invention were successfully synthesized individually on resin in parallel with the library construction. Each was subsequently cleaved by stirring the resin for 4 hr in TFA:methylene chloride (7:3). The resin was removed by filtering the suspension through glass wool. Volatiles were then removed from the filtrate in vacuo to give the crude carboxylic acid product. Treatment of each product with excess (trimethylsilyl)diazomethane gave the methyl ester, which was then purified by flash chromatography. The structures of the recovered ligands were confirmed by $^1$H NMR and mass spectroscopy. These two compounds served as quality controls for the integrity of both the bulk reagents and the reaction conditions during library synthesis.

EXAMPLE 3

DECODING PROCEDURE

A bead is placed in a 1.3 mm diameter pyrex capillary with 2 µL of acetonitrile. Ceric ammonium nitrate solution (2 µL of a 0.1M aq. solution) and hexane (3 µL) are added and the two-phase mixture centrifuged briefly. The tube is sealed and left at 35° C. for 16 hrs, then opened. The organic layer is removed by syringe and mixed with 1 µL of N,O-bis(trimethylsilyl)acetamide. The silated tag solution (1 µL) is analyzed by GC with electron capture (EC) detection.

The GC analysis is performed with a Hewlett Packard 5890 plus gas chromatograph. On column injection into a 5 m, 0.32 mm retention gap connected to a 25 m, 0.2 mm crosslinked 5% phenylmethyl silicone column is used. The temperature and pressure programs for the analysis are 200°–320° C., 15° C./min, then 320° C for 10 min and 20–40 psi at 2 psi/min, then 40 psi for 10 min. The EC detector is maintained at 400° C. and the auxiliary gas is set at 35 psi.

The identity of the library compound attached to the bead is ascertained based on the reagents utilized in the synthesis of such compound, which are readily determined from the binary codes associated, respectively, with each of the identifiers for such reagents, as characterized through the above procedure. The binary codes for the identifiers assigned to the various reagents are represented in the following tables.

TABLE 1-1

Aa₁ Reagents and Encoding Scheme

| Aa₁ Reagent | Binary Code |
|---|---|
| 1. 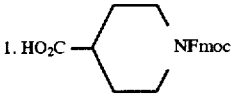 | 001 |
| 2.  | 010 |
| 3.  racemic | 011 |
| 4. 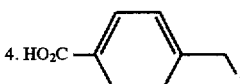 | 100 |
| 5. 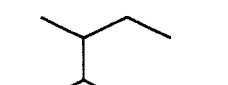 | 101 |
| 6. 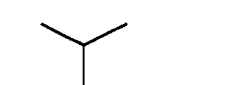 | 110 |
| 7. 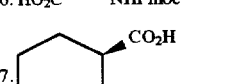 | 111 |

TABLE 1-2

Aa₂ Reagents and Encoding Scheme

| Aa₂ Reagent | Binary Code |
|---|---|
| 1. 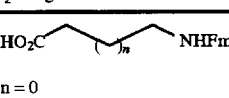 n = 0 | 0001 |
| 2.  n = 1 | 0010 |
| 3. 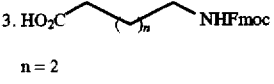 n = 2 | 0011 |
| 4.  n = 3 | 0100 |
| 5. 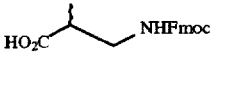 | 0101 |

TABLE 1-2-continued

Aa₂ Reagents and Encoding Scheme

| Aa₂ Reagent | Binary Code |
|---|---|
| 6. 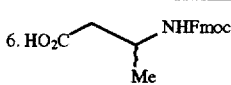 HO₂C—CH(Me)—NHFmoc | 0110 |
| 7.  HO₂C—CH(CF₃)—NHFmoc | 0111 |
| 8. 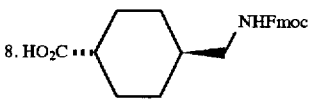 HO₂C-cyclohexyl-CH₂NHFmoc | 1000 |
| 9. 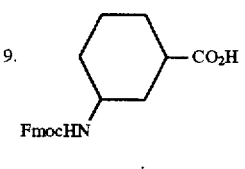 FmocHN-cyclohexyl-CO₂H (racemic) | 1001 |
| 10. 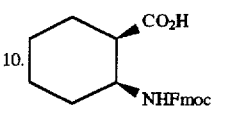 cyclohexyl with CO₂H and NHFmoc | 1010 |
| 11. 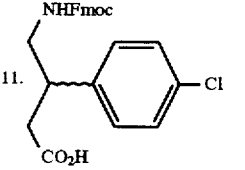 4-Cl-C₆H₄-CH(CH₂NHFmoc)(CH₂CO₂H) | 1011 |
| 12. 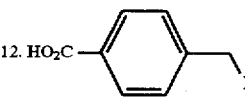 HO₂C-C₆H₄-CH₂NHFmoc | 1100 |
| 13. 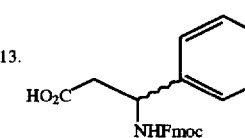 HO₂C-CH₂-CH(Ph)-NHFmoc | 1101 |
| 14. 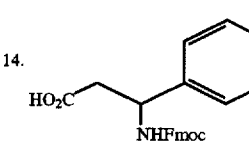 HO₂C-CH₂-CH(4-Cl-C₆H₄)-NHFmoc | 1110 |
| 15. 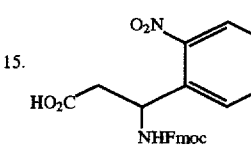 HO₂C-CH₂-CH(2-O₂N-C₆H₄)-NHFmoc | 1111 |

TABLE 1-3

Benzaldehyde and Heteroaromatic Carboxaldehyde Reagents and Encoding Scheme

| Aldehyde Reagent | Binary Code |
|---|---|
| 1. 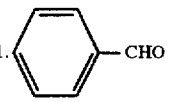 C₆H₅-CHO | 00001 |
| 2. 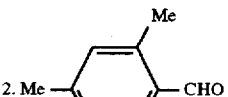 2,4-dimethyl-C₆H₃-CHO | 00010 |
| 3. 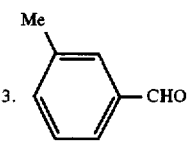 3-Me-C₆H₄-CHO | 00011 |
| 4. 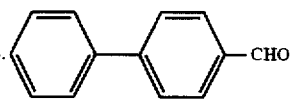 4-biphenyl-CHO | 00100 |
| 5. 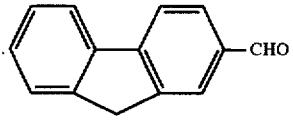 fluorene-2-CHO | 00101 |
| 6. 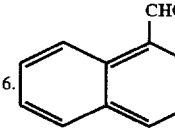 1-naphthaldehyde | 00110 |
| 7. 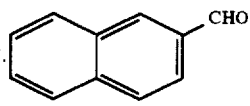 2-naphthaldehyde | 00111 |
| 8. 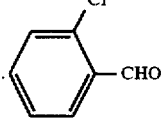 2-Cl-C₆H₄-CHO | 01000 |
| 9. 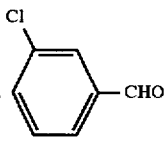 3-Cl-C₆H₄-CHO | 01001 |
| 10. 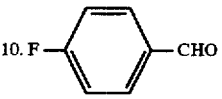 4-F-C₆H₄-CHO | 01010 |
| 11. 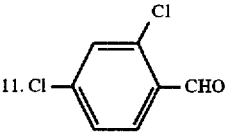 2,4-diCl-C₆H₃-CHO | 01011 |

TABLE 1-3-continued

Benzaldehyde and Heteroaromatic Carboxaldehyde Reagents and Encoding Scheme

| Aldehyde Reagent | Binary Code |
|---|---|
| 12. 3-Cl, 4-Cl-C6H3-CHO | 01100 |
| 13. 3-HO-C6H4-CHO | 01101 |
| 14. 3-HO, 4-HO-C6H3-CHO | 01110 |
| 15. 2-OMe-C6H4-CHO | 01111 |
| 16. 3-MeO-C6H4-CHO | 10000 |
| 17. 3-BnO-C6H4-CHO | 10001 |
| 18. 4-BuO-C6H4-CHO | 10010 |
| 19. 3-MeO, 4-MeO-C6H3-CHO | 10011 |
| 20. 3-HO, 4-MeO-C6H3-CHO | 10100 |
| 21. 3-(PhO)-C6H4-CHO | 10101 |
| 22. 4-(3-Cl-C6H4-O)-C6H4-CHO | 10110 |
| 23. 4-(3,4-Cl2-C6H3-O)-C6H4-CHO | 10111 |
| 24. 4-NC-C6H4-CHO | 11000 |
| 25. pyridine-2-CHO | 11001 |
| 26. pyridine-3-CHO | 11010 |
| 27. pyridine-4-CHO | 11011 |
| 28. furan-2-CHO | 11100 |
| 29. furan-3-CHO | 11101 |
| 30. thiophene-2-CHO | 11110 |
| 31. thiophene-3-CHO | 11111 |

TABLE 1-4
Epoxides
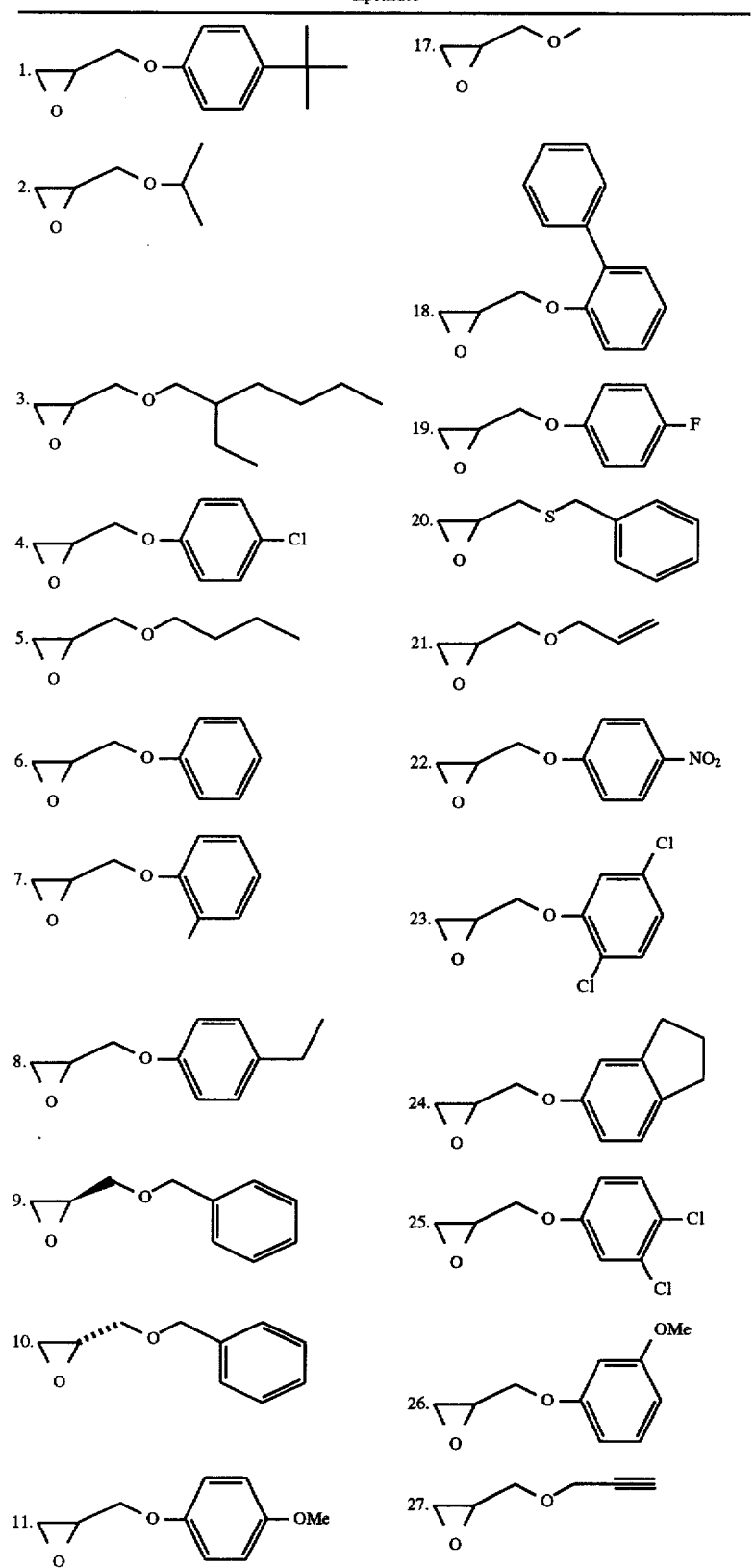

TABLE 1-4-continued

Epoxides

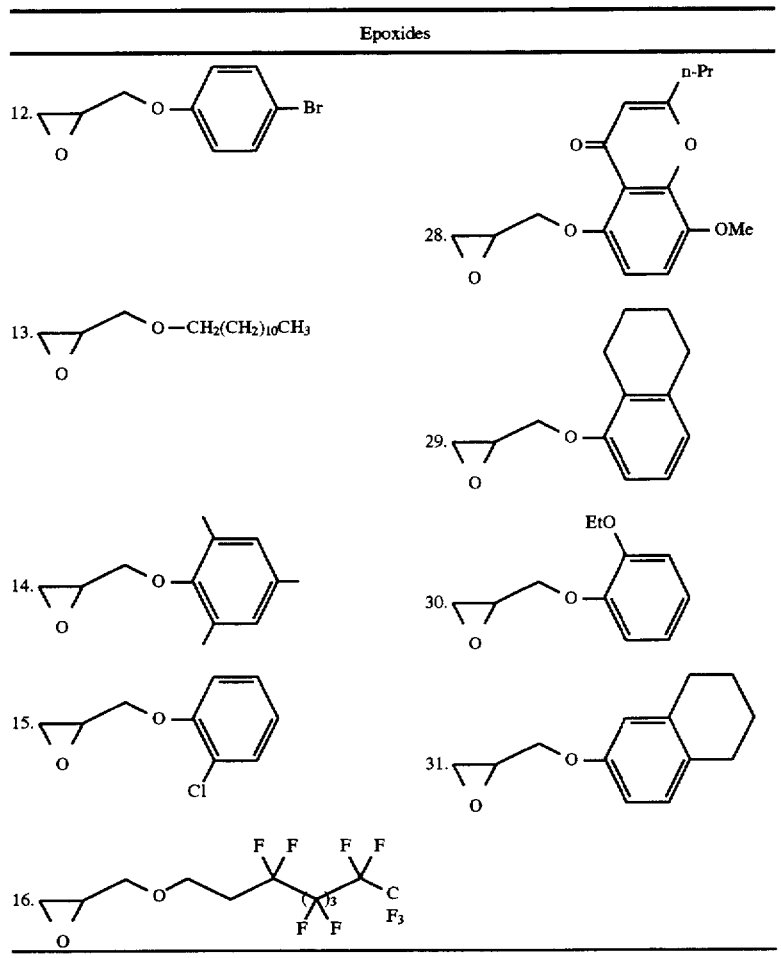

What is claimed is:

1. A combinatorial chemical library for biological screening, comprising a plurality of members of the formula:

$$(T-L)_q - \text{\textcircled{S}} - C(O) - L' - II''\quad I$$

or $$\text{\textcircled{S}} - C(O) - L' - II''\quad I'$$

wherein:

\textcircled{S} is a solid support;

q is 2-30;

L is a first linker;

L' is a second linker;

T' is a tag; and together T'-L- form an identifier residue;

II' is an attached ligand of formula

-Aa$^1$-Aa$^2$-(CH$_2$Ar$^1$)-CH$_2$CHOH-CH$_2$XR$^1$ wherein:

Aa$^1$ and Aa$^2$ is each an amino acid joined to each other through an amide bond with the provisos that Aa$^1$ cannot contain a linear chain of 3, 4, or 5 atoms which separate the carboxyl carbonyl from the amino group of Aa$^1$, and Aa$^2$ cannot be an α-amino acid;

Ar$^1$ is aryl or heteroaryl;

—CH$_2$Ar$^1$ is attached to N on Aa$^2$;

R$^1$ is H, C$_{1-20}$ alkyl, alkenyl, alkynyl, aryl, heteroaryl, substituted aryl or heteroaryl, aryl or heteroaryl fused to a 3- or 4-membered moiety to form a non-aromatic second ring, or substituted C$_{1-20}$ alkyl, alkenyl, or alkynyl; and X is O, N-loweralkyl, S, S(O), or S(O)$_2$.

2. A library of claim 1 wherein:

T'-L- is of the Formula:

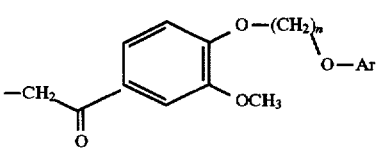

wherein:

n=3-12;

Ar is halophenyl; and q is 3-12.

3. A library of claim 1 wherein:
-L'- is

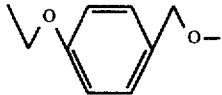
(a)

wherein the left-hand bond as shown is the point of attachment to the solid support and the right hand bond is the point of attachment to the ligand.

4. A library of claim 2 wherein in Formula III: 1) n=3-12 and Ar is pentachlorophenyl; or 2) n=5-6 and Ar is 2,4,6-trichlorophenyl.

5. A library of claim 1 wherein:
Aa$^1$ is a de-protected amino acid of Table 1-1;
Aa$^2$ is a de-protected amino acid of Table 1-2;
Ar$^1$ is an aldehyde residue of a compound of Table 1-3;
CH$_2$XR$^1$ is a desepoxide compound of Table 1-4; and X is O or S.

6. A combinatorial library of chemical intermediates comprising a plurality of members of the formula:

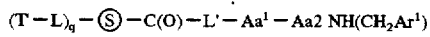

or

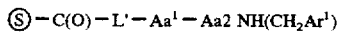

wherein:

Ⓢ is a solid support;
q is 2-30;
L is a first linker;
L' is a second linker;
T' is a tag; and
together T'-L- form an identifier residue;

Aa$^1$ is the residue of an amino acid, other than 4-aminobutanoic acid, 5-aminopentanoic acid and 6-aminohexanoic acid, attached to L' via its carboxyl and to Aa2NH via its amino;

Aa2NH is the residue of an amino acid, other than an α-amino acid, attached to Aa$^1$ via its carboxyl and to CH$_2$Ar$^1$ via its amino; and Ar$^1$ is aryl or heteroaryl.

* * * * *

UNITED STATES PATENT AND TRADEMARK OFFICE
CERTIFICATE OF CORRECTION

PATENT NO. : 5,766,963
DATED : June 16, 1998
INVENTOR(S) : Baldwin et al.

It is certified that error appears in the above-identified patent and that said Letters Patent is hereby corrected as shown below:

[54] Title, and col. 1,   "COMBINATION" should read --COMBINATORIAL--.

Column 35, line 46,   "(T-L)q" should read --(T'-L)q--.

Signed and Sealed this

Third Day of November, 1998

Attest:

BRUCE LEHMAN

Attesting Officer          Commissioner of Patents and Trademarks